United States Patent [19]

Frances et al.

[11] Patent Number: 5,075,468

[45] Date of Patent: Dec. 24, 1991

[54] OPTIONALLY CHELATED TIN(IV) COMPOUNDS USEFUL AS LATENT CATALYSTS

[75] Inventors: Jean-Marc Frances, Villeurbanne; Veronique Gouron, Talence; Bernard Jousseaume, Talence; Michel Pereyre, Talence, all of France

[73] Assignee: Rhone-Poulenc Chimie, Courbevoie, France

[21] Appl. No.: 591,744

[22] Filed: Oct. 2, 1990

[30] Foreign Application Priority Data

Oct. 2, 1989 [FR] France .................. 89 13057

[51] Int. Cl.$^5$ .............................. C07F 7/22
[52] U.S. Cl. ........................ 556/87; 556/88; 556/89; 528/18; 528/44
[58] Field of Search ............ 556/81, 87, 88, 89; 528/18, 44

[56] References Cited

U.S. PATENT DOCUMENTS

| | | |
|---|---|---|
| 4,427,695 | 1/1984 | Ehr . |
| 4,456,559 | 6/1984 | Drabek .................. 556/87 |
| 4,785,124 | 11/1988 | Campbell et al. ......... 556/87 X |
| 4,826,672 | 5/1989 | Milius et al. ........... 556/87 X |

FOREIGN PATENT DOCUMENTS 0232541  8/1987  European Pat. Off. .
0298877  1/1989  European Pat. Off. .

OTHER PUBLICATIONS

Chemical Abstracts, vol. 88, 1978, p. 133, Resume No. 70106e, Columbus, Ohio U.S.; W. N. Aldridge et al., "Action on Mitochondria and Toxicity of Metabolites of Tri-n-butyltin Derivatives", & Biochem Pharmacol 1977, 26(21) 1997–2000, *Abrege; 2-butanol, 1-(-dibutylchlorostannyl)-RN[65301-76-0].

Journal or Organometallic Chemistry, vol. 118, No. 1, 28 Sep. 1976, pp. 41–54; R. H. Fish et al., "Bioorganotin Chemistry: Reactions of Tributyltin Derivatives with a Cytochrome P-450 Dependent Monoxygenase Enzyme System", *P. 44, equations (6,7)*.

Primary Examiner—Arthur C. Prescott
Attorney, Agent, or Firm—Burns, Doane, Swecker & Mathis

[57] ABSTRACT

Optionally chelated tetracoordinated or pentacoordinated tin(IV) compounds having the general formula:

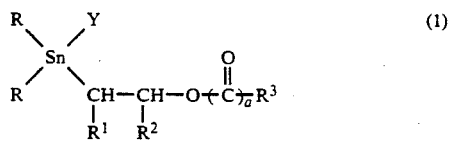

are useful latent catalysts in compositions for the preparation of polyurethanes, or for the crosslinking of organopolysiloxanes, by increasing the temperature of appropriate reaction mixtures to a level above the decomposition temperature of such tin(IV) compound.

16 Claims, No Drawings

OPTIONALLY CHELATED TIN(IV) COMPOUNDS USEFUL AS LATENT CATALYSTS

BACKGROUND OF THE INVENTION

1. Field of the Invention

The present invention relates to tetracoordinated or pentacoordinated tin(IV) compounds useful, in particular, as latent catalysts in the preparation of polyurethanes and for the crosslinking of organopolysiloxanes.

2. Description of the Prior Art

Numerous tin compounds are known to this art which are useful as catalysts, in particular for:

(i) the synthesis of polyurethanes; exemplary thereof are the tin chelates (U.S. Pat. No. 3,055,845) and the products of the reaction between a tin(IV) carboxylate and a sulfonylisocyanate (DE-A-3,326,566 and EP-A-232,541);

(ii) the crosslinking of silicone polymers by a polycondensation reaction; exemplary thereof are the dialkyl-tin dicarboxylates (Noll, *Chemistry and Technology of Silicones*, page 337, Academic Press, 1968—2nd edition), and the dialkyl-tin bischelates (EP-A-147,323 and U.S. Pat. No. 4,517,337).

Tetracoordinated tin(IV) compounds useful as latent catalysts ar described in published French Patent Applications 88/05,554 and 88/05,555, filed Apr. 21, 1988 and assigned to the assignee hereof.

SUMMARY OF THE INVENTION

A major object of the present invention is the provision of a novel class of tetracoordinated or pentacoordinated tin(IV) compounds which are both inactive at ambient temperature (about 20° C.), in particular for the two applications indicated above, but which are converted into active species by increasing the temperature above ambient.

This type of compound is typically termed a "latent catalyst".

Briefly, the present invention features latent catalysts having the general formula:

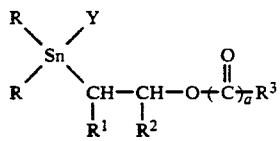
(1)

in which the radicals R, which may be identical or different, are each a straight or branched chain $C_1-C_{20}$ alkyl radical, a single-ring aryl radical, or an arylalkyl or alkylaryl radical in which the alkyl moiety is $C_1-C_6$; the radicals $R^1$ and $R^2$, which may be identical or different, are each a hydrogen atom, a cyano radical, a $C_1-C_6$ alkyl radical, or an alkoxycarbonyl radical in which the alkyl moiety is $C_1-C_6$, with the proviso that $R^1$ and $R^2$ may together form a saturated hydrocarbon ring having from 5 to 8 carbon atoms; the radical $R^3$ is a hydrogen atom, a straight or branched chain $C_1-C_{20}$ alkyl radical, a straight or branched chain $C_1-C_{20}$ alkoxy radical, a single-ring aryl radical or a single-ring aryloxy radical; a is 0 or 1; and the radical Y is a hydrogen atom, a halogen atom, a straight or branched chain $C_1-C_{20}$ alkoxy radical, a straight or branched chain $C_1-C_{20}$ acyloxy radical or a chelate group of the formula:

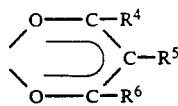
(2)

wherein the radicals $R^4$ and $R^6$, which may be identical or different, are each a radical R or a $C_1-C_5$ alkoxy radical; and the radical $R^5$ is a hydrogen atom or a radical $R^4$, or $R^4$ forms with $R^5$ a divalent $C_5-C_{12}$ cyclic hydrocarbon radical.

DETAILED DESCRIPTION OF THE PREFERRED EMBODIMENTS OF THE INVENTION

More particularly according to the present invention, R is preferably a butyl, octyl or 2-ethylhexyl radical and the two radicals R are identical; $R^1$ is H; $R^2$ is H; a=1; $R^3$ is a methyl, ethyl or undecyl radical; and Y is H, Cl, acetoxy, lauroyloxy or acetylacetonate.

The preferred compounds corresponding to the formula (1) are the following:

(i) 2-acetoxyethyl-dibutyl-tin chloride:
R=butyl, $R^1=R^2=H$, $R^3=$methyl,
Y=Cl, a=1;

(ii) 2lauroyloxyethyl-dibutyl-tin chloride:
R=butyl, $R^1=R^2=H$, $R^3=$undecyl,
Y=Cl, a=1;

(iii) 2-ethoxyethyl-dibutyl-tin chloride:
R=butyl, $R^1=R^2=H$, $R^3=$ethyl,
Y=Cl, a=0;

(iv) 2-acetoxyethyl-dibutyl-tin acetate:
R=butyl, $R^1=R^2=H$, $R^3=$methyl,
Y=acetoxy, a=1;

(v) 2-lauroyloxyethyl-dibutyl-tin laurate:
R=butyl, $R^1=R^2=H$, $R^3=$undecyl,
Y=lauroyloxy, a=1;

(vi) 2-acetoxyethyl-dibutyl-tin acetylacetonate:
R=butyl, $R^1=R^2=H$, $R^3=$methyl,
Y=acetylacetonate (pent-2-en-4-one-2-oxy),
a=1;

(vii) 2-lauroyloxyethyl-dibutyl-tin acetylacetonate:
R=butyl, $R^1=R^2=H$, $R^3=$undecyl,
Y=acetylacetonate (pent-2-en-4-one-2-oxy),
a=2;

(viii) 2-acetoxyethyl-dibutyl-tin hydride:
R=butyl, $R^1=R^2=Y=H$, $R^3=$methyl,
a=1;

(ix) 2-lauroyloxyethyl-dibutyl-tin hydride:
R=butyl, $R^1=R^2=Y=H$, $R^3=$undecyl,
and a=1.

The compounds of formula (1) where Y is H can be prepared by an addition reaction, preferably of a large molar excess of a diorgano-tin dihydride of formula (3):

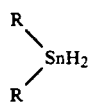 (3)

in which the radicals R, which may be identical or different, are as defined above in respect of formula (1), with an analogous derivative of formula (4):

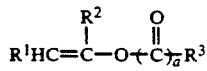 (4)

in which the radicals $R^1$, $R^2$ and $R^3$ are also as defined above in respect of formula (1).

The hydrides of formula (1) where Y is H are thus obtained, in general as a mixture with at least 20% by weight of the tin compound of formula

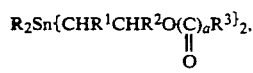

where R, $R^1$, $R^2$, $R^3$ and a are also as defined above in respect of formula (1).

The majority of the dihydrides of formula (3) are known compounds and are widely described in the literature. In the event where these are new compounds, they are prepared, for example, by reduction of the corresponding diorgano-tin dichloride using lithium aluminum hydride.

Another suitable such process entails reducing the corresponding diorgano-tin oxide with a polydiorganosiloxane bearing a SiH function, such as, for example, a polyhydrogenomethylsiloxane blocked at each end of the polyme chain by a trimethylsilyl group.

The majority of the carboxylates and alcoholates of formula (4) are also known compounds and described in the literature; they are otherwise easily prepared.

Thus, for example, the vinyl carboxylates of the formula:

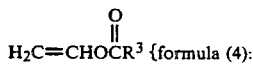 {formula (4):

$R^1 = R^2 = H$) are prepared by transesterification of vinyl acetate with the acid $R^3COOH$ in an acid medium.

The enol carboxylates of the formula:

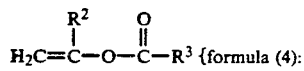 {formula (4):

$R_1 = H$, $R_3 = CH_3$) are prepared by reacting the ketone $H_3C-COR^2$ with isopropenyl acetate in an acid medium.

The hydrostannation reaction of a compound of formula (3) with a compound of formula (4) is preferably carried out by reacting at least three moles of compound of formula (3) with two moles of compound of formula (4) at ambient temperature in an organic hydrocarbon solvent such as anhydrous cyclohexane. The reaction mixture is subjected to UV radiation (360 nm).

The hydrostannation reaction can also be carried out without solvent in the presence of a compound generating free radicals, such as, for example, in the presence of AIBN (azobisisobutyronitrile) at a temperature of 70° to 80° C.

The tin halides of formula (1) where Y is a halogen atom, preferably chlorine, can be prepared by one of the following two methods:

(i) a first method comprising carrying out the halogenation of the corresponding hydride of formula (1) where Y=H using a halogenating agent, which in the event that a chlorination is oarried out is advantageously carbon tetrachloride, in accordance with the reaction:

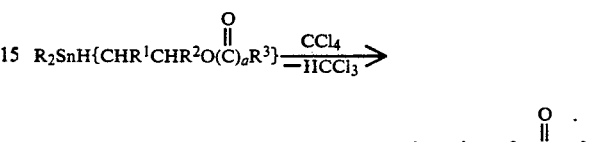

(ii) a second method comprising carrying out the addition reaction of the diorgano-tin halogenohydride of the formula:

 (5)

where, Y represents a halogen atom and R is as defined in formula (1), with the enol derivative of formula (4).

The halide of formula (1) is thus obtained quantitatively. The reaction can be carried out at ambient temperature in solution in an organic solvent such as anhydrous cyclohexane, under UV radiation (360 nm).

The halohydride of formula (5) is obtained quantitatively by reaction of an equimolar mixture of dihydride of formula (3) with a corresponding diorgano-tin dihalide.

The tin compounds of formula (1) where Y is an alkoxy, acyloxy or chelate radical can be obtained by replacing the halogen atom of the corresponding tin halide of formula (1) by the alkoxy, acyloxy or chelate group of an organometallic salt of the formula: wherein Y is an alkoxy, acyloxy or chelate radical corresponding to the definition given above for formula (1) and M is a monovalent metal such as $Na^+$, $K^+$, $Li^+$, $Ag^+$ or a quaternary ammonium.

The reaction, which is generally quantitative, is preferably carried out in an organic hydrocarbon solvent such as toluene at ambient temperature.

The tin compounds of formula (1), which are generally liquids at ambient temperature, can be identified by the IR (infrared) and NMR ($^{119}Sn$, $^{13}C$ and $^1H$ nuclear magnetic resonance) spectroscopy analytical techniques as well as by mass spectroscopy and by measurement of the MOSSBAUER effect.

However, it is found that, in the current state of the art of analytical techniques, the $^{119}Sn$ NMR analytical method, as described in particular in an article by Peter J. Smith, "CHEMICAL SHIFTS OF $^{119}Sn$ NUCLEI IN ORGANOTIN COMPOUNDS", page 291 et seq., published in *ANNUAL REPORTS OF NMR SPECTROSCOPY*, volume 8, 1978 ACADEMIC PRESS, is a method which is itself sufficiently accurate to characteri·e the various tin compounds present in a mixture, in parucular a reaction mixture, and to enable the chemical formulae of most of these compounds to be determined.

The fundamental parameter evaluated by $^{119}$Sn NMR is the value of the chemical shift expressed in parts per million relative to a reference (generally tetramethyltin).

The value of the ohemical shift $\delta$ is, in particular, sensitive to the electronegativity of the groups borne by the tin and to the variation in the coordination number of the tin atom. Specific studies on the characterization of organostannic derivatives using $^{119}$Sn NMR are described, in particular, by A. G. Davies and P. J. Smith, *COMPREHENSIVE ORGANO-METALLIC CHEMISTRY* 11 *TIN*, pages 523 to 529 and by J. Otera, *J. OF ORGANOMET. CHEM.*, 221, pages 57–61 (1981).

The compounds of formula (1) are stable at ambient temperature and, at ambient temperature (25° C.), are inactive as catalysts for the preparation of polyurethanes and as catalysts for the curing of organopolysiloxane compositions.

On the other hand, the compounds of formula (1) are useful as catalysts for the preparation of polyurethanes and as catalysts for the curing of organopolysiloxane compositions after thermal decomposition thereof in the reaction mixtures to be catalyzed.

Indeed, the compounds of formula (1), when subjected to elevated temperatures, undergo thermal decomposition to catalytically active compounds according to the mechanism:

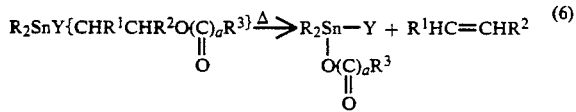

(6)

The thermal decomposition of the compounds of formula (1) occurs at a temperature which is specific for each of such compounds. This temperature generally ranges from 40° to 250° C.

The compounds of formula (6) thus liberated are active catalysts for the preparation of polyurethanes and/or the curing of polyorganosiloxane compositions.

One advantage of the latent catalysts of formula (1) is, therefore, to be able to mix the starting materials with the latent catalyst without catalysis of the reaction taking place and to initiate the catalysis of the reaction by heating the mixture to the decomposition temperature of the latent catalyst.

This decomposition temperature, which generally ranges from 40° to 250° C., can be decreased by the addition of an effective amount of a nucleophilic agent selected from among, for example, water, a secondary organic amine, an organic alcohol, an organosilicon compound containing a silanol function and an organic compound containing a mercapto (SH) function. By "effective amount" is intended 0.001 mole to 10 moles or more of nucleophilic agent per mole of compound of formula (1).

The present invention, therefore, also features a process for the preparation of polyurethanes, according to which an organic polyisocyanate, an organic compound containing at least two groups containing active hydrogen and a catalytically effective amount of a latent catalyst of formula (1) are mixed at ambient temperature and the mixture is brought at least to the thermal decomposition temperature of the latent catalyst.

The latent catalyst is preferably used in a concentration of 0.001 to 6 parts, preferably 0.01 to 1 part by weight, calculated as weight of metallic tin, per 100 parts by weight of the solids content of the starting reactants.

The polyisocyanates and the organic compounds containing at least two group containing active hydrogen are well known to this art. They are described, for example, in U.S. Pat. No. 3,055,845 and EP-A-232,541.

The "pot life" time of the reaction mixture is identical whether or not a latent catalyst of formula (1) is present in such mixture. This "pot life" is at least three times longer than that which is observed for a reaction mixture containing an equimolar amount of active catalyst corresponding to that obtained by decomposition of the latent catalyst of formula (1).

The catalysis is initiated as soon as the reaction mixture is brought to a temperature at least equal to the decomposition temperature of the latent catalyst. The reactivity observed is then similar to that obtained by the use of an equimolar amount of the corresponding active catalyst.

Thus, the present invention also features a process for crosslinking a polyorganosiloxane composition, according to which a polydiorganosiloxane (A) having silanol endgroups, a polyorganohydrogenosiloxane (B) and a catalytically effective amount of a latent catalyst (C) of formula (1) are mixed and the mixture is brought to a temperature equal to or higher than the thermal decomposition temperature of the latent catalyst, with evaporation of the solvent or the water present in the mixture, if appropriate.

More specifically, such polyorganosiloxane composition typically comprises:

(A) 100 parts by weight of a polydiorganosiloxane having silanol endgroups;

(B) 0.1 to 25 parts by weight of a polyorganohydrogenosiloxane having at least 3 SiH groups pe molecule; and (C) a catalytically effective amount of a latent catalyst of formula (1); wherein the SiH:SiOH molar ratio ranges from 0.6 to 10.

The organic radicals of the polymers (A) and (B) are preferably $C_1$–$C_6$ alkyl radicals or phenyl radicals, at least 80% by number being methyl radicals.

The decomposition temperature of the catalyst generally ranges from 30° to 200° C. It depends on the particular latent catalyst used and on the form of the polyorganosiloxane composition.

This decomposition temperature can be lowered by the addition of an effective amount of a nucleophilic agent selected, for example, from among water, a secondary organic amine, an organic alcohol, an organosilicon compound containing a silanol function and an organic compound containing a mercapto (SH) function. By "effective amount" of nucleophilic agent is intended from 0.001 to 10 moles or more of nucleophilic agent per mole of tin compound of formula (1).

Thus, for the polyorganosiloxane compositions without solvent and in solution in an organic solvent, this decomposition temperature is close to the specific intrinsic decomposition temperature of the latent catalyst. For these two types of compositions it is often possible to formulate the compositions in a single packaging having a storage stability time which can be longer than 6 months.

On the other hand, for the compositions in aqueous emulsion, this decomposition temperature can be decreased to ambient temperature in certain cases. It is then generally desirable to formulate the emulsion in at least two packagings for storage. In this case, the "pot life" time of the composition is substantially improved relative to that of the compositions containing a known tin catalyst. This "pot life" is, for example, three times longer than that observed with a composition without solvent containing an equimolar amount of dibutyltin diacetylacetonate.

According to the invention, by "effective amount of latent catalyst" is generally intended a concentration of 0.001 to 6 parts, preferably of 0.01 to 3 parts (calculated as weight of tin metal) of latent catalyst of formula (1) per 100 parts by weight of the solids content of the sum of the polymers (A) and (B).

The coating compositions according to the invention do not generally contain inorganic fillers. However, the presence of fillers, preferably siliceous (precipitated silica, silica obtained by combustion, diatomaceous earths, ground quartz, etc.), generally used in silicone elastomer compositions is not excluded to a concentration of 1 to 50 parts of filler to 100 parts of polymer (A), in particular for producing thin coatings from a few μm to several mm thick.

The polymers (A) and (B) have long been known to this art.

The polymers (A) can be selected from among the polydimethylsiloxanes having terminal hydroxyl groups (having silanol endgroups), having a viscosity of at least 10 mPa.s at 25° C. These polymers (A) comprise oils of low viscosity ranging, for example, from 10 mPa.s to 5,000 mPa.s, viscous oils having a viscosity from 5,000 to $10^6$ mPa.s and gums having a viscosity greater than $10^6$ mPa.s.

The polymers (B) can be straight-chain, cyclic or branched.

The viscosity of the polymers (B) ranges from 2 mpa.s at 25° C. to 10,000 mpa.s at 25° C.

In the case where the composition is used without solvent, the viscosity of the polymers (A) and (B) is selected such that the viscosity of the mixture, namely, of the composition, ranges from 40 to 5,000 mPa.s, preferably from 100 to 3,000 mPa.s at 25° C.

The compositions according to the invention can be emulsified, dispersed or diluted in water or dissolved in a volatile organic solvent compatible with the composition, selected, for example, from among the alkanes, the petroleum cuts containing paraffin compounds, toluene, heptane, xylene, isopropanol, methyl isobutyl ketone, tetrahydrofuran, chlorobenzene. chloroform, 1,1,1-trichloroethane and the derivatives of monoethylene glycol and of methylene glycol.

Preferably, at the point in time of actual use the water or the solvent constitutes from 50% to 99% by weight of the dispersion or the solution.

The composition hardens during the crosslinking treatment which entails the evaporation of the water or the solvent; it is therefore useful as a coating composition for flexible supports made of metal, paper, plastic material, cardboard, etc.

The compositions according to the invention can also be used as compositions for rendering a material, such as metal foils, glass, plastic materials or paper, nonadherent to other materials to which it would normally adhere.

In order to further illustrate the present invention and the advantages thereof, the following examples are given, it being understood that same are intended only as illustrative and in nowise limitative.

In-said examples to follow, all of the products analyzed by NMR were diluted in deuterated benzene unless otherwise indicated. The chemical shifts are indicated in ppm.

EXAMPLE 1

Preparation and Decomposition of 2-acetoxvethyl-dibutyl-tin chloride:

(a) Preparation: a stoichiometric solution of chlorodibutyltin hydride and vinyl acetate in anhydrous cyclohexane was exposed to UV at 30° C. under nitrogen for 1 hour. At the end of the reaction, the solvent was removed under vacuum, at ambient temperature.

Spectral characteristics: $^1$H (pure) NMR δ: 4.2 (2H, t); 1.7 (3H, s); 1.6–0.9 (20H, m); $|^3J(^{117}Sn^1H)|=81$ Hz; $|^3J(^{119}Sn^1H)|=85$ Hz $^{119}$Sn NMR δ: 74.6.

(b) Decomposition: at the end of 1 hour, 15 minutes, at 90° C. the product was decomposed to chlorodibutyltin acetate.

Spectral characteristics: $^1$H NMR δ: 2.0–0.8 (m) $^{119}$Sn NMR δ: −28 (wide).

EXAMPLE 2

Preparation and Decomposition of 2-lauroyloxyethyl-dibutyl-tin chloride (a) Preparation: the operating procedure of Example 1 was repeated, except that the exposure lasted 2 hours and that vinyl acetate was replaced by vinyl laurate.

Spectral characteristics: $^1$H (pure NMR δ: 4.15 (2H, t); 2.2–0.9 (43H, m); $|^3J(^{117}Sn^1H)|=81$ Hz and $|^3J(^{119}Sn^1H)|=85$ Hz.

(b) Decomposition: at the end of 2 hours at 90° C., the product was completely decomposed to chlorodibutyltin laurate.

Spectral characteristics: $^1$H NMR δ: 2.2 (2H, t); 1.7–0.8 (39H, m) $^{119}$Sn NMR δ: −29 (wide).

EXAMPLE 3

Preparation and Decomposition of 2-ethoxyethyl-dibutyl-tin chloride (A) Preparation: the operating procedure of Example 1 was repeated, except that the exposure lasted 3 hours at 5° C. and that vinyl acetate was replaced by vinyl ethyl ether.

Spectral characteristics: $^1$H NMR δ: 3.5–2.9 (4H, m); 1.8–0.8 (23H, m) $|^3J$ (SnH)$|=66$ Hz $^{119}$Sn NMR δ: 103.6.

(b) Decomposition: at the end of 1 hour, 20 minutes, at 150° C., the product was completely decomposed to ethoxychlorodibutyltin.

Spectral characteristics: $^1$H NMR δ: 3.9 (2H, q); 1.8–0.9 (21H, m) $^{119}$Sn NMR δ: −113.0.

EXAMPLE 4

Preparation and Decomposition of 2-acetoxyethyl-dibutyl-tin acetate (a) Preparation: a large excess of silver acetate was added to a solution of 2-acetoxyethyldibutyl-tin chloride in anhydrous toluene. The mixture was stirred for 15 minutes at ambient temperature and then filtered. The solvent was then removed under vacuum.

Spectral characteristics; $^1$H (pure) NMR δ: 4.4 (2H, m); 2.0 (3H, s); 1.95 (3H, s); 1.6–0.9 (20H, m) $|^3J$ (SnH)$|=77$ Hz, (b) Decomposition: at the end of 1 hour at 75° C., the product was completely decomposed into dibutyltin diacetate.

Spectral characteristics: $^1$H NMR δ: 2.0 (6H, s); 1.65–0.9 (18H, m) $^{119}$Sn NMR δ: −156.3 IR ν (CO): 1,605, 1,570, 1,425 cm$^{-1}$ (F).

EXAMPLE 5

Preparation and Decomposition of 2-lauroyloxyethyl-dibutyl-tin laurate (a) Preparation: the same operating procedure as in Example 4 was repeated, except that the starting chloride was 2-lauroyloxyethyl-dibutyl-tin chloride. The replacement was effected using potassium laurate.

Spectral characteristics: $^1$H NMR δ: 4.4 (2H, m); 2.0–0.9 (66H, m); $^{119}$Sn NMR δ: 35.9.

(b) Decomposition: at the end of 2 hours at 75° C., the product had completely disappeared to yield dibutyltin dilaurate.

Spectral characteristics: $^1$H NMR δ: 2.2 (4H, t); 1.6–0.9 (60H, m) $^{119}$Sn NMR δ: −152.5.

EXAMPLE 6

Preparation and Decomposition of 2-acetoxyethyl-dibutyl-tin acetylacetonate (a) Preparation: the operating procedure of Example 4 was repeated, except that the replacement was effected using potassium acetylacetonate.

Spectral characteristics: $^1$H NMR δ: 5.3 (1H, s) 4.4 (2H, m); 2.0 (3H, s); 1.8 (6H, s); 1.7–0.9 (20H, m) $|^3J(^{117}Sn^1H)|$=68 Hz $^{119}$Sn NMR δ: 38.8.

(b) Decomposition: at the end of 1 hour at 120° C., the product was completely decomposed to a mixture of dibutyltin diacetylacetonate, dibutyltin diacetate and dibutyltin acetylacetonate acetate.

Spectral characteristics: $^{119}$Sn NMR δ: −260 (wide); −155 (dibutyltin diacetate) −400 (very wide, dibutyltin diacetylacetonate).

EXAMPLE 7

Preparation and Decomposition of 2-lauroyloxyethyl-dibutyl-tin acetylacetonate (a) Preparation: the operating procedure of Example 5 was repeated, except that the replacement was effected using potassium acetylacetonate.

Spectral characteristics: $^1$H NMR δ: 5.35 (1H, s); 4.4 (2H, m); 2.20 (2H, t); 1.85 (6H, s); 1.5–0.9 (41H, m) $^{119}$Sn NMR δ: 39.6.

(b) Decomposition: at the end of 3 hours at 120° C., the product had completely disappeared to yield a mixture of the same type as that obtained in Example 6.

Spectral characteristics: $^{119}$Sn NMR δ: −263 (wide); −151.4 (dibutyltin dilaurate) −400 (very wide) dibutyltin diacetylacetonate).

EXAMPLE 8

Preparation and Decomposition of 2-acetoxyethyl-dibutyl-tin hydride:

(a) Preparation: a solution of 11.6 mmoles of vinyl acetate, 6.3 g (26.8 mmoles) of dibutyltin dihydride and 1.8 g of anhydrous cyclohexane, placed under nitrogen in a pyrex vessel thermostat-controlled at 20° C., was exposed to UV for two hours. The excess stannic dihydride and the solvent were removed under a substantial vacuum (10$^{-5}$ KPa), at ambient temperature. The analyses of the product indicated that the hydride (1) was obtained as a mixture with 20% to 30% of Bu$_2$Sn(CH$_2$CH$_2$OCOCH$_3$)$_2$.

Spectral characteristics: $^1$H (pure) NMR δ: 5.0 (1H, m); 4.3 (2H, m); 1.8 (3H, s); 1.5–0.9 (20H, m); $|^3J(SnH)|$=38 Hz $^{119}$Sn NMR δ: −100.0 IR (film) : ν (SnH)=1,840 cm$^{-1}$ (F).

(b) Decomposition: at the end of 3 hours at 110° C., the hydride was completely decomposed to active catalyst.

EXAMPLE 9

Preparation and Decomposition of 2-lauroyloxyethyl-dibutyl-tin hydride (a) Preparation: the operating procedure of Example 8 was repeated, except that vinyl acetate was replaced by vinyl laurate.

Spectral characteristics: $^1$H (pure) NMR δ: 5.0 (1H, m); 4.4 (2H, m); 2.3 (2H, t); 1.6–0.9 (41H, m); $|^3J(SnH)|$=39 Hz $^{119}$Sn NMR δ: −99.50.

(b) Decomposition: at the end of 4 hours at 110° C., the hydride was completely decomposed to active catalyst.

EXAMPLE 10

Use of Latent Catalyst for the Preparation of Polyurethanes

Preparation of a reaction mass: by mixing a diol, a diisocyanate and an organostannic compound.

Reagents (i) the diol used was a mixture of butane-1,4-diol and polyether of molecular weight 1,000, each chain end of which had a OH function;

(ii) the diisocyanate used was IPDI: isocyanato-3-methyl-3,5,5-trimethyl-cyclohexyl isocyanate of the formula:

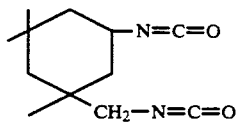

(iii) the organostannic compound was used in a proportion of 0.03 part of compound per 100 parts by mass (of solids) of the diol and IPDI.

Operating method: the following materials were introduced into a vacuum flask:

(i) 5.26 g of polyether,
(ii) 0.8 g of butane-1,4-diol.

The mixture was degassed and 1 ml of a solution containing 0.63 mmol of organostannic compound in 25 ml of anhydrous ether was introduced.

The solvent was evaporated under vacuum and 3.94 g of IPDI were added.

The final reaction mixture was degassed for 2 minutes.

Two reaction mixtures were produced: one containing the latent catalyst 2-lauroyloxyethyl-dibutyl-tin acetylacetonate termed C$_1$ and the other containing a known catalyst, termed C$_2$, namely, dibutyltin diacetylacetonate. A third mixture was produced without catalyst. Each mixture was divided into two batches. The gel time ("pot life" time) at ambient temperature (27° C.) was determined on a first batch and the time necessary to solidify to a gel at 140° C. was determined on the second batch.

The results are reported in Table I below.

TABLE I

| "Sn" | WITHOUT CATALYST | CATALYST C₁ | CATALYST C₂ |
|---|---|---|---|
| "pot life" time at 27° C. | 6 hours | 2 hours | 40 minutes |
| time to solidify to a gel at 140° C. | 21 minutes | 5 minutes | 4 minutes, 30 seconds |

It will be seen from Table I that the "pot life" time at ambient temperature of the mixture containing the latent catalyst was three times longer than that of the mixture containing the catalyst. At 140° C. the latent catalyst very rapidly recovered all of its activity, since this preparation required no more time to gel than that containing the catalyst.

EXAMPLE 11

Use of Latent Catalyst for Crosslinking an Organopolysiloxane Composition

The following mixture was homogenized in ambient air:

(i) 23 g of α,ω-dihydroxypolydimethylsiloxane oil having a viscosity of 5,000 mPa.s;

(ii) 1 g of a polyhydrogenomethylsiloxane oil containing dimethylsilyl endgroups and having a viscosity of 20 mPa.s;

(iii) SiH/SiOH molar ratio=9;

(iv) 0.178 millimole of organostannic compound.

A first mixture contained 2-lauroyloxyethyl-dibutyl-tin acetylacetonate, termed C₁, as the organostannic compound.

A second mixture contained dibutyltin diacetylacetonate, termed C₂, as the organostannic compound.

Each of these two mixtures was divided into two batches.

On the first two batches, the stability of the mixtures in ambient air was determined by measuring the time necessary for each of the mixtures to reach 150,000 mPa.s at 29° C. A CARRI-MED ® rheometer on which a cone/plate system thermostat-controlled at 29° C. was fitted was used for this purpose.

On the second two batches, the crosslinking time at 150° C. for a composition having a thickness of 10 mm was measured.

The results obtained are reported in Table II below.

TABLE II

| | CATALYST C₁ | CATALYST C₂ |
|---|---|---|
| "Pot life" time at 29° C. | 2 hours, 30 min | 50 minutes |
| Crosslinking time at 150° C. | 10 minutes | 10 minutes |

It will be seen from Table II that the "pot life" time in ambient air was almost 3 times longer with C₁ than with C₂, for an analogous crosslinking time at 150 ° C.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A tetracoordinated or pentacoordinated tin(IV) compound having the general formula:

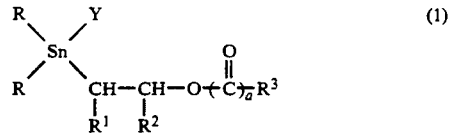

in which the radicals R, which may be identical or different, are each a straight or branched chain $C_1$-$C_{20}$ alkyl radical, a single-ring aryl radical, or an arylalkyl or alkylaryl radical in which the alkyl moiety has from 1 to 6 carbon atoms; the radicals $R^1$ and $R^2$, which may be identical or different, are each a hydrogen atom, a cyano radical, a $C_1$-$C_6$ alkyl radical, or an alkoxycarbonyl radical in which the alkyl moiety has from 1 to 6 carbon atoms, with the proviso that $R^1$ and $R^2$ may together form a saturated hydrocarbon ring having 5 to 8 carbon atoms; the radical $R^3$ is a hydrogen atom, a straight or branched chain $C_1$-$C_{20}$ alkyl radical, a straight or branched chain $C_1$-$C_{20}$ alkoxy radical, a single-ring aryl radical or a single-ring aryloxy radical; a is 0 or 1; and the radical Y is a hydrogen atom, a halogen atom, a straight or branched chain $C_1$-$C_{20}$ alkoxy radical, a straight or branched chain $C_1$-$C_{20}$ acyloxy radical or a chelate group of the formula:

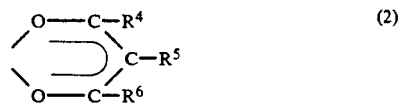

wherein the radicals $R^4$ and $R^6$, which may be identical or different, are each a radical R or a $C_1$-$C_5$ alkoxy radical, and the radical $R^5$ is a hydrogen atom or a radical $R^4$, or $R^4$ forms with $R^5$ a divalent $C_5$-$C_{12}$ cyclic hydrocarbon radical, with the proviso that when $R^3$ is hydrogen a is equal to 1.

2. The tin(IV) compound as defined by claim 1, wherein R is a butyl, octyl or 2-ethylhexyl radical and the two radicals R are identical; $R^1$ is H; $R^2$ is H; a=1; $R^3$ is a methyl, ethyl or undecyl radical; and Y is H, Cl, acetoxy, lauroyloxy or acetylacetonate.

3. The tin(IV) compound as defined by claim 1, the same being 2-acetoxyethyl-dibutyl-tin chloride (R=butyl, $R^1$=$R^2$=H, $R^3$=methyl, Y=Cl, a=1).

4. The tin(IV) compound as defined by claim 1, the same being 2-lauroyloxyethyl-dibutyl-tin chloride (R=butyl, $R^1$=$R^2$=H, $R^3$=undecyl, Y=Cl, a=1).

5. The tin(IV) compound as defined by claim 1, the same being 2-ethoxyethyl-dibutyl-tin chloride (R=butyl, $R^1$=$R^2$=H, $R^3$=ethyl, Y=Cl, a=0).

6. The tin(IV) compound as defined by claim 1, the same being 2-acetoxyethyl-dibutyl-tin acetate (R =butyl, $R^1$=$R^2$=H, $R^3$=methyl, Y=acetoxy, a=1).

7. The tin(IV) compound as defined by claim 1, the same being 2-lauroyloxyethyl-dibutyl-tin laurate (R=butyl, $R^1$=$R^2$=H, $R^3$=undecyl, Y=lauroyloxy, a=1).

8. The tin(IV) compound as defined by claim 1, the same being 2-acetoxyethyl-dibutyl-tin acetylacetonate (R=butyl, $R^1$=$R^2$=H, $R^3$=methyl, Y=acetylacetonate (pent-2-en-4-one-2-oxy), a=1).

9. The tin(IV) compound as defined by claim 1, the same being 2-lauroyloxyethyl-dibutyl-tin acetylacetonate (R=butyl, $R^1=R^2=H$, $R^3=$undecyl, Y=acetylacetonate (pent-2-en-4-one-2-oxy), a=1).

10. The tin(IV) compound as defined by claim 1, the same being 2-acetoxyethyl-dibutyl-tin hydride (R=butyl, $R^1=R^2=Y=H$, $R^3=$methyl, a=1).

11. The tin(IV) compound as defined by claim 1, the same being 2-lauroyloxyethyl-dibutyl-tin hydride (R=butyl, $R^1=R^2=Y=H$, $R^3=$undecyl and a=1).

12. A process for releasing a catalytically active compound having the formula:

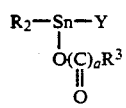

(6)

comprising thermally decomposing the tin(IV) compound as defined by claim 1.

13. The process as defined by claim 12, carried out in the presence of an effective decomposition temperature reducing amount of a nucleophilic agent.

14. The process as defined by claim 13, said nucleophilic agent comprising water, a secondary organic amine, an organic alcohol, an organosilicon compound bearing a silanol function or an organic compound bearing a mercapto (SH) function.

15. A polymerizable composition of matter comprising an organic polyisocyanate, an organic compound containing at least two groups bearing active hydrogen atoms and a polymerization initiating amount at elevated temperatures, of the tin(IV) compound as defined by claim 1.

16. A curable organopolysiloxane composition of matter, comprising a polydiorganosiloxane having silanol endgroups, a polyorganohydrogenosiloxane and an effective crosslinking amount, at elevated temperatures, of the tin(IV) compound as defined by claim 1.

* * * * *